(12) United States Patent
Castán Barberán et al.

(10) Patent No.: US 10,583,079 B2
(45) Date of Patent: Mar. 10, 2020

(54) COMPOSITION FOR SKIN HYGIENE AND/OR HYDRATION

(71) Applicant: KAO CORPORATION, S.A., Barcelona (ES)

(72) Inventors: Pilar Castán Barberán, Barcelona (ES); Judit Rodríguez Costero, Barcelona (ES)

(73) Assignee: KAO CORPORATION, S.A., Barbera del Valles-Barcelona (ES)

( * ) Notice: Subject to any disclaimer, the term of this patent is extended or adjusted under 35 U.S.C. 154(b) by 1280 days.

(21) Appl. No.: 14/394,436

(22) PCT Filed: Apr. 15, 2013

(86) PCT No.: PCT/ES2013/070237
§ 371 (c)(1),
(2) Date: Oct. 14, 2014

(87) PCT Pub. No.: WO2013/156647
PCT Pub. Date: Oct. 24, 2013

(65) Prior Publication Data
US 2015/0118328 A1 Apr. 30, 2015

(30) Foreign Application Priority Data
Apr. 16, 2012 (ES) .................................. 201200412

(51) Int. Cl.
| A61K 8/92 | (2006.01) |
| A61Q 19/10 | (2006.01) |
| A61K 8/39 | (2006.01) |
| A61K 8/06 | (2006.01) |
| A61K 8/37 | (2006.01) |
| A61Q 19/00 | (2006.01) |

(52) U.S. Cl.
CPC .............. *A61K 8/922* (2013.01); *A61K 8/062* (2013.01); *A61K 8/37* (2013.01); *A61K 8/39* (2013.01); *A61Q 19/007* (2013.01); *A61Q 19/10* (2013.01); *A61K 2800/59* (2013.01); *A61K 2800/5922* (2013.01)

(58) Field of Classification Search
None
See application file for complete search history.

(56) References Cited

U.S. PATENT DOCUMENTS

| 4,130,497 A | 12/1978 | Oneto et al. |
| 4,371,548 A | 2/1983 | Hermann et al. |
| 6,132,738 A | 10/2000 | Lerg et al. |
| 6,290,944 B1 * | 9/2001 | Garnier ................. A61K 8/365 424/70.1 |
| 6,306,410 B1 | 10/2001 | Doki |
| 2005/0124705 A1 * | 6/2005 | Schreiber ............. A61K 8/0208 516/53 |
| 2006/0165616 A1 | 7/2006 | Brock et al. |

FOREIGN PATENT DOCUMENTS

| DE | 10261110 A1 | 7/2004 |
| EP | 1045021 A1 | 10/2000 |
| EP | 1411892 B1 | 2/2002 |
| EP | 1213007 A2 | 6/2002 |
| EP | 2438904 A1 | 10/2010 |

OTHER PUBLICATIONS

International Search Report, dated Sep. 26, 2013.
"Cosmetic and dermatologic formulations containing the polymeric rheology modifier Polyurethane-39," IP.CO Journal, IP.COM Inc., 2009.

* cited by examiner

Primary Examiner — Terry A McKelvey
Assistant Examiner — Catheryne Chen
(74) Attorney, Agent, or Firm — Tristan A. Fuierer; Olive Law Group, LLC

(57) ABSTRACT

The present invention relates to a composition for cleansing and/or moisturizing skin. The compositions of the invention which provide a cosmetic or dermatological composition for cleansing and/or moisturizing skin, preferably compositions used for showering or bathing, comprise:
  a) at least one alkyl ether carboxylate,
  b) at least one ethoxylated glycerol ester,
  c) at least one oily substance,
  d) water,
  e) optionally one or more emulsifiers,
  f) optionally additional surfactants, and
  g) optionally cosmetically or pharmaceutically acceptable excipients or active ingredients;
characterized by containing a minimum of 20% by weight, preferably 30% by weight, of component (c) with respect to the total weight of the active material of the composition. Additionally, the invention provides a method for cleansing and/or moisturizing skin using the compositions of the invention.

14 Claims, No Drawings

COMPOSITION FOR SKIN HYGIENE AND/OR HYDRATION

CROSS-REFERENCE TO RELATED APPLICATIONS

This application is filed under the provisions of 35 U.S.C. § 371 and claims the priority of International Patent Application No. PCT/EP2013/070237 filed on 15 Apr. 2013 entitled "COMPOSITION FOR SKIN HYGIENE AND/OR HYDRATION" in the name of Pilar CASTÁN BARBERÁN, et al., which claims priority to Spanish Patent Application No. P201200412 filed on 16 Apr. 2012, both of which are hereby incorporated by reference herein in their entirety.

FIELD OF THE ART

The present invention relates to cosmetic or dermatological compositions for cleansing and/or moisturizing skin, particularly to cosmetic or dermatological compositions for cleansing and/or moisturizing skin when bathing or showering, characterized by their high oil content and low water content.

STATE OF THE ART

Skin cleansing process can cause certain skin aggressions that can produce slight swelling on its outermost layer. This surface irritation is generally compensated by the skin own protection mechanisms. However, in the case of skin that is prone to drying or is subjected to certain deterioration due to the effect of factors such as sunlight or the cold, such natural protection mechanisms may not be enough. For this reason, in addition to the mildest possible cleansing agents, the formulations used as body wash must contain specific components, such as oils for example, which are added for the purpose of skin protection.

One of such formulations for cleansing skin that meets such requirement are the so-called shower oils. Such composition is characterized by containing a mixture of mild surfactants combined with oils present in relatively high proportions. Said compositions gently cleanse the skin and, as a result of the oils, relax, soften and protect the skin from drying.

The main technical difficulty in obtaining shower oils is the solubilization of the relatively high percentage of required oil in the surfactant system, in other words, in obtaining stable, preferably transparent, single-phase formulations which are further capable of producing suitable foam in terms of quantity and quality.

The use of triisopropanolamine (TIPA) lauryl ether sulphate to overcome such technical difficulty is well known. For example, document U.S. 61/32,738A describes a cosmetic or dermatological shower preparation containing fatty alcohol sulphates and fatty alcohol ether sulphates, preferably TIPA laureth sulphate, oil selected from lipids containing one to three acyl radicals esterified using an alcohol, water and optionally other additives.

The state of the art includes some alternatives to the TIPA lauryl ether sulphate-based system.

U.S. Pat. No. 4,371,548 describes a bath or shower composition consisting of a mixture of surfactants (10% to 90% by weight of amine (C8-C18) fatty alcohol sulphate optionally ethoxylated in the (C8-C18) fatty alcohol sulphate anion, where the amines are preferably mixtures of diethylamine and monobutylethanolamine, and a metal or an ammonium ethoxylated (C8-18) fatty alcohol sulphate with a cosmetically acceptable oil (20% to 60% by weight).

U.S. Pat. No. 4,130,497 describes a single liquid phase cosmetic composition which can be used for bath and for shower and which provides the skin with a film of a skin benefit agent which is retained after the bath or shower. Said composition contains oil and a mixture of anhydrous anionic surfactants, the first surfactant being an anhydrous amine salt of (C8-C18) fatty alcohol sulphate, containing on average 0 to 4 moles of ethylene oxide, preferably mono- or diethyl ethanolamine of lauryl ether sulphate with 2 or 3 moles of ethylene oxide, diethylamine and monobutylethanolamine of lauryl ether sulphate and the amine of nonylphenyl and octylphenyl sulphate, and the second surfactant being an alkyl ether carboxylic acid or a sodium or amine salt thereof.

Finally, document U.S. Pat. No. 6,306,410 is relevant to the present invention. This document describes single-phase, transparent cosmetic compositions for removing make-up that can be easily spread and removed using water. The compositions contain up to 80% by weight of oily bodies and ethoxylated partial glycerides.

DESCRIPTION OF THE INVENTION

In the field of cosmetic and dermatological compositions for cleansing skin, particularly in the field of bath preparations and especially shower preparations, there is a need to provide cleansing compositions with a high content of oil solubilized in the surfactant system, such compositions therefore being stable, preferably transparent, single-phase compositions which are capable of providing a high degree of oil deposition on skin, suitable foam production, good application capability and a satisfactory cleansing ability.

The present invention offers an efficient solution to the requirements mentioned above by providing a cosmetic or dermatological composition comprising:

a) at least one alkyl ether carboxylate,
b) at least one ethoxylated glycerol ester,
c) at least one oily substance,
d) water,
e) optionally one or more emulsifiers,
f) optionally additional surfactants, and
g) optionally cosmetically or pharmaceutically acceptable excipients or active ingredients;

characterized by containing a minimum of 20% by weight, preferably 30% by weight, of component (c) with respect to the total weight of the active material of the composition of the invention.

The shower or bath compositions according to the invention are transparent, allow a good oil deposition on skin, have foaming ability and are non-irritating.

The present invention also provides a method for cleansing and/or moisturizing skin comprising the steps of (1) wetting or dampening the skin; (2) applying a sufficient amount of a composition according to the present invention on the skin and, finally, (3) rinsing the skin with water.

The present invention also provides the use of a composition according to invention for cleansing and/or moisturizing skin, particularly for cleansing and/or moisturizing skin when showering or bathing.

The present invention also provides a method for the preparation of the compositions of the invention.

DETAILED DESCRIPTION OF THE INVENTION

The compositions of the invention providing a cosmetic or dermatological composition for cleansing and/or moisturizing skin, preferably compositions used for showering or bathing, comprise:
- a) at least one alkyl ether carboxylate,
- b) at least one ethoxylated glycerol ester,
- c) at least one oily substance,
- d) water,
- e) optionally one or more emulsifiers,
- f) optionally additional surfactants, and
- g) optionally cosmetically or pharmaceutically acceptable excipients or active ingredients;

characterized by containing a minimum of 20% by weight, preferably 30% by weight, of component (c) with respect to the total weight of the active material of the composition of the invention.

a) Alkyl Ether Carboxylates

The composition of the invention comprises a component (a) comprising at least one alkyl ether carboxylate.

The alkyl ether carboxylates according to the invention are described in accordance with the following formula (I)

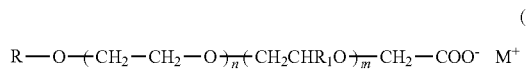

wherein
R is a linear or branched, saturated or unsaturated alkyl or alkenyl group having 6 to 22 carbon atoms
$R_1$ is an alkyl group having 1 to 4 carbon atoms
n has a value in the range of 0 to 20
m has a value in the range of 0 to 6
$M^+$ is a cation preferably selected from the group consisting of hydrogen, an alkaline metal, an alkaline earth metal, ammonium, an alkylammonium, an alkanolammonium or a glucammonium.

In one embodiment of the invention, the ether carboxylates can be ethoxylated and propoxylated, the value of n and of m in formula (I) therefore being greater than 0. The order or sequence of the ethylene oxide and propylene oxide groups is not critical for the invention. Therefore, both the ether carboxylates according to formula (I) containing ethylene oxide and propylene oxide in separate blocks and those ether carboxylates according to formula (I) where ethylene oxide and propylene oxide are randomly distributed can be used in the compositions according to the invention.

However, in a preferred embodiment of the invention the ethers carboxylates of formula (I) are free of propylene oxide. Examples of commercially available alkyl ether carboxylates of formula (I) free of propylene oxide are those corresponding to the commercial reference AKYPO® RLM 45 CA (INCI name Laureth-6 Carboxylic Acid) and AKYPO® RO 20 (INCI name Oleth-3 Carboxylic Acid), AKYPO® RLM 25 (INCI name Sodium Laureth-6 Carboxylate), AKYPO® RLM 45N (INCI name Sodium Laureth-6 Carboxylate), AKYPO® RLM 100 (INCI name Laureth-11 Carboxylic Acid), AKYPO® LF-1 (INCI name Capryleth-6 Carboxylic Acid), AKYPO® LF-2 (INCI name Capryleth-9 Carboxylic Acid), AKYPO® RO50 (INCI name Oleth-6 Carboxylic Acid), AKYPO® RO90 (INCI name Oleth-10 Carboxylic Acid), marketed by KAO Chemicals Europe.

In a preferred embodiment of the invention, alkyl ether carboxylates with an alkyl chain R containing between 6 and 22 carbon atoms are preferred, more preferably between 10 and 18; with a value of n between 1 and 15, preferably between 1 and 6; and with a value of m between 0 and 3, preferably between 0 and 2, more preferably m is 0.

In a preferred embodiment of the invention, the ether carboxylate of formula (I) is characterized by an alkyl chain R containing between 10 and 14 carbon atoms, n between 3 and 6 moles of ethylene oxide per mole of alkyl ether carboxylate and m is equal to 0.

In another preferred embodiment of the invention, the ether carboxylate of formula (I) is characterized by an alkyl chain R containing between 16 and 18 carbon atoms, n between 1 and 5 moles of ethylene oxide per mole of alkyl ether carboxylate, preferably n between 1 and 3 and m equal to 0.

b) Ethoxylated Glycerol Esters

The present invention comprises an ethoxylated glycerol ester (component (b)) having the formula (II).

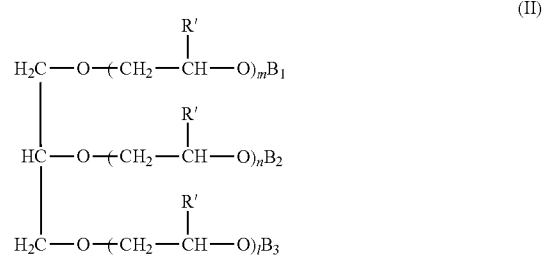

where said formula (II) comprises the components of formula i), ii), iii) and/or iv),
- i) being the component represented by formula (II), where one of the symbols $B_1$, $B_2$, $B_3$ independently represents an acyl group represented by —CO—R and the rest represents H
- ii) being the component represented by formula (II) where two of the symbols $B_1$, $B_2$, $B_3$ independently represent an acyl group represented by —CO—R and the rest represents H;
- iii) being the component represented by formula (II) where each of the symbols $B_1$, $B_2$, $B_3$ independently represents an acyl group represented by —CO—R;
- iv) being the component represented by formula (II), where each of $B_1$, $B_2$ and $B_3$ represents H;

each of m, n or l independently represents a number from 0 to 40, the sum of m, n, l being in the range of 1 to 40;
R' represents H or $CH_3$, preferably H;
characterized in that in the acyl group represented by —CO—R, R represents a linear or branched alkyl or alkenyl group having 3 to 21 carbon atoms, preferably 5 to 17 carbon atoms, more preferably 5 to 11 carbon atoms.

In a preferred embodiment of the invention, component b) according to invention comprises at least two different components of formula (II): one of formula (I), (ii) or (iii), and another of formula (Iv); the proportion of the components [(i)+(ii)+(iii)]/(iv) by weight being between 3.0:0.3 and 0.5:3.0.

In a more preferred embodiment of the invention, component b) according to invention comprises components of formulas (i), (ii), (iii) and (iv); the proportion of the components [(i)+(ii)+(iii)]/(iv) by weight being between 3.0:0.3 and 0.5:3.0, and the ratio of the components (i)/(ii)/(iii) by weight being 60-90/10-35/less than 10.

Particularly, in the acyl group represented by —CO—R of formula (II), R preferably represents an alkyl or alkenyl group having 5 to 9 carbon atoms.

In addition, the degree of alkoxylation, i.e., the sum of m, n and l is preferably comprised between 1 and 20, more preferably between 5 and 12, still more preferably between 5 and 9.

In a preferred embodiment of the invention, component (b) preferably comprises at least one component of each formula (i), (ii), (iii) or (iv); the R of the group —CO—R represents an alkyl group having 5 to 9 carbon atoms; the degree of ethoxylation, i.e., the sum of m, n and l is comprised between 5 and 9 and finally, the proportion of [(i)+(ii)+(iii)]/(iv) by weight is in the range of 2.0:0.5 to 0.5:3, preferably of 1.5:0.8 to 0.8:2.5.

Examples of commercially available ethoxylated glycerol esters according to the invention are those corresponding to the commercial reference Emanon-EVE (INCI name Glycereth-7 Caprate/Caprylate), Levenol® C-201 (INCI name Glycereth-17 Cocoate), Levenol® C-301 (INCI name Glycereth-7 Cocoate), Levenol® C-421 (INCI name Glycereth-2 Cocoate), Levenol® H&B (INCI name Glycereth-2 Cocoate), Levenol® N-242 (INCI name PEG-6 Caprylic/Capric Glycerides), Levenol® N-661 (INCI name Glycereth-7 Caprylate/Caprate)

c) Oily Substance

The present invention comprises a component (c) comprising at least one oily substance.

The oily substances according to the invention are defined as cosmetically acceptable and substantially water immiscible liquids at room temperature. The oily substance of the invention can comprise natural oils defined as the fatty acid glyceryl esters (triglycerides) naturally occurring in animal or plant tissues, including those which have been hydrogenated to reduce or eliminate unsaturations. The oily substance of the invention can also include synthetic oils obtained from glycerol and fatty acid preparations.

The oily substances can be selected, among others, from animal or plant oils, hydrocarbons, esters of a higher alcohol and a higher fatty acid, fatty acids, triglycerides, fatty acid cholesterol esters, scented oils and mixtures of any of the aforementioned components.

In a preferred embodiment of the present invention, component c) is a plant oil. Examples of plant oils according to the invention are soya bean oil, palm oil, rapeseed oil, sunflower oil, wheat germ oil, coconut oil, olive oil, castor oil, safflower oil, peanut oil, palm kernel oil, cottonseed oil, corn oil, grapeseed oil, hazelnut oil, linseed oil, rice bran oil, sesame oil or mixtures thereof.

Particularly, the oils of the invention are preferably chosen from soya bean oil, sunflower oil, castor oil and wheat germ oil, or mixtures thereof.

The Composition of the Invention

The compositions according to the invention provide a cosmetic or dermatological composition for cleansing and/or moisturizing skin, preferably compositions used for showering or bathing, comprising:
a) at least one alkyl ether carboxylate,
b) at least one ethoxylated glycerol ester,
c) at least one oily substance,
d) water,
e) optionally one or more emulsifiers,
f) optionally additional surfactants, and
g) optionally cosmetically or pharmaceutically acceptable excipients or active ingredients;

characterized by containing a minimum of 20% by weight, preferably 30% by weight, of component (c) with respect to the total weight of the active material of the composition of the invention.

Active material is understood as the group of specific components responsible for a specific action; in the scope of the present application, i.e., of a cosmetic or dermatological skin cleansing and/or moisturizing composition, the active material is all the surfactants present in the composition. In the scope of the present invention, all the surfactants is understood as the sum of components a, b and f.

In a preferred embodiment of the invention, the compositions according to the invention comprise:
between 10% and 34%, preferably between 13% and 21%, of component a)
between 9% and 30%, preferably between 20% and 28%, of component b), and
between 20% and 50%, preferably between 30% and 45%, of component c);
each of the indicated amounts being expressed as percentage by weight of the mentioned component with respect to the total weight of the active material of the composition.

The proportion of component (a) and component (b) by weight is preferably comprised between 0.3:1 and 4:1.

In addition, the proportion of component (a) and component (c) by weight is preferably comprised between 0.3:1 and 0.9:1.

Finally, the proportion of component (b) and component (c) is preferably comprised between 0.2:1 and 0.8:1.

A cosmetic or dermatological composition for cleansing and/or moisturizing skin is preferred, preferably compositions used for showering or bathing, comprising:
between 10% and 34%, preferably between 13% and 21% of a component (a) comprising an alkyl ether carboxylate of formula (I) with an alkyl chain R containing between 10 and 14 carbon atoms, n between 3 and 6 and m equal to 0.
between 9% and 30%, preferably between 20% and 28%, of a component (b) comprising at least one ethoxylated glycerol ester in accordance with formula (II), where the R group of the —CO—R group represents an alkyl group having 5 to 9 carbon atoms, and the degree of ethoxylation, i.e., the sum of n, m and l is comprised between 5 and 9.
between 30% and 45% of at least one component c) comprising at least one oily substance, preferably soya bean oil, sunflower oil, castor oil, wheat germ oil or mixtures thereof,
each of the percentages being calculated with respect to the total weight of the active material of said composition.

A cosmetic or dermatological composition for cleansing and/or moisturizing skin is preferred, preferably compositions used for showering, comprising, with respect to the total weight of the active material of said composition:
between 10% and 34%, preferably between 13% and 21%, of a component (a) comprising at least one alkyl ether carboxylate with an alkyl chain containing between 16 and 18 carbon atoms, n between 1 and 5, and m equal to 0.
between 9% and 30%, preferably between 20% and 28%, of a component (b) comprising at least one ethoxylated glycerol ester in accordance with formula (II), where the R group of the —CO—R group represents an alkyl group having 5 to 9 carbon atoms, and the degree of ethoxylation, i.e., the sum of n, m and l is comprised between 5 and 9.

between 30% and 45% of at least one component c) comprising at least one oily substance, preferably soya bean oil, sunflower oil, castor oil, wheat germ oil or mixtures thereof.

The pH of the bath or shower compositions according to the invention is preferably comprised between 5 and 6.5.

The compositions of the invention also contain water (component d)). The water used is distilled water. The minimum water content is 1% by weight with respect to the total composition. Furthermore, the compositions of the invention optionally contain one or more emulsifiers (component e)), additional surfactants (component f)) and cosmetically or pharmaceutically acceptable excipients or active ingredients (component g)). A non-limiting list of the mentioned optional components is included below:

Emulsifiers such as glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidic alcohol, behenyl alcohol, isobehenyl alcohol, selachyl alcohol, chimyl alcohol, polyethylene glycol(2) stearyl ether (INCI name Steareth-2), glyceryl monolaurate.

Surfactants. Mild surfactants especially compatible with skin are fatty alcohol polyglycolethersulphates, monoglyceridesulphates, mono- and/or di-alkyl sulfosuccinates, fatty acid isethionates, fatty acid sarcosinates, fatty acid taurides, fatty acid glutamates, alkyl oligoglucosides, fatty acid glucamides, alkyl amido betaines and/or protein fatty acid condensates.

Cosmetically or Pharmaceutically Acceptable Excipients

Hydrotopes such as short chain alkyl aryl sulfonates, sulfosuccinates.

Thickening agents that are suitable according to the present invention are hydrophilic silicas, polysaccharides, more particularly: cellulose, guar gum, starch, "pullulan" (α-1,4-;α-1,6-glucan), "dextran", "fructan", "mannan" ("glucomannan"), agar, "carrageenan", chitin, chitosan, pectin, alginic acid, and hyaluronic acid; and the derivatives thereof having substituent groups such as methyl groups, ethyl groups, hydroxyethyl groups, hydroxypropyl groups or the like; polysaccharide derivatives such as hydroxyethyl cellulose, hydroxyethyl ethylcellulose, hydroxyethyl guar gum, hydroxyethyl starch, methyl cellulose, methyl guar gum, methyl starch, ethyl cellulose, ethyl guar gum, ethyl starch, hydroxypropyl cellulose, hydroxypropyl guar gum, hydroxypropyl starch, hydroxyethyl methyl cellulose, hydroxyethyl methyl guar gum, hydroxyethyl methyl starch, hydroxypropyl methyl cellulose, metal hydroxypropyl guar gum, and hydroxypropyl methyl starch; high molecular weight fatty acids polyethylene glycol monoesters and diesters; polyacrylates; polyacrylamides; polyvinyl alcohol and polyvinylpyrrolidone; fatty acid esters with polyols, such as pentaerithritol, ethylene glycol or trimethylol propane, optionally ethoxylated, such as ethoxylated pentaerithritol stearate (INCI name PEG-150 Pentaerythritol Tetrastearate) or polyethylene glycol stearate (INCI name PEG-150 Distearate); alkyl oligoglucosides; ethoxylated fatty amides, such as for example, ethoxylated amide of rapeseed fatty acid corresponding to the INCI name PEG-4 Rapeseedamide; amides of alkyl ether carboxylic acids, such as for example, that corresponding to the INCI name Trideceth-2 Carboxamide MEA.

Other excipients that the invention can contain are perfumes, solubilizers, silicones, deodorants, anti-microbial substances, complexing agents, cationic polymers, anionic polymers, amphoteric polymers and non-ionic polymers, preservatives, plant extracts, vitamins, antioxidants.

Cosmetically or pharmaceutically acceptable active ingredients that the invention can contain are, for example, aloe vera, pyrithione zinc, urea, etc.

In another embodiment, the invention provides a method for cleansing and/or moisturizing skin comprising the steps of:

(1) wetting or dampening the skin (2) applying a sufficient amount of a composition according to the present invention on the skin. The composition of the present invention can be applied directly on the skin or can be applied on the skin by means of a cleansing instrument. Examples of cleansing instruments include, in a non-exclusive manner, brushes, sponges and meshes; and finally (c) rinsing the skin with water.

In another embodiment, the invention provides the use of a composition according to the invention for cleansing and/or moisturizing, particularly for cleansing and/or moisturizing skin when showering or bathing.

In another embodiment, the invention provides the use of a composition according to the invention for the preparation of a cosmetic or dermatological composition for cleansing and/or moisturizing skin, particularly for cleansing and/or moisturizing skin when showering or bathing.

In a last embodiment, the invention provides a method for the preparation of the compositions of the invention which comprises first mixing components a), b) and c), and optionally e), f) and g); adjusting the pH with a NaOH solution and finally adding water.

EXAMPLES

Table 1 shows the compositions A, B and C prepared for comparison purposes, as well as Examples D to G which correspond to compositions according to the invention.

The compositions are obtained by mixing the surfactant components with the corresponding oils and propylene glycol. The pH of the composition is adjusted with NaOH (50%) and finally the addition of water is compensated for. In the case of formulas containing alkyl ether carboxylic acid (i.e., the compositions according to the invention) it is convenient to avoid neutralizing the acid before ending the formulation because it can cause turbidity. The mixture of the components of the formulas occurs at room temperature and under constant stirring.

The data found in Table 1 represent the percentages by weight of active material (% AM).

TABLE 1

| Component | A | B | C | D | E | F | G |
|---|---|---|---|---|---|---|---|
| Zetesol TP 3001 | 32.2 | — | — | — | — | — | — |
| Akypo RLM 45 CA[2] | — | — | 41.9 | 32.2 | — | 17.7 | 12.7 |
| Akypo RO-20[3] | — | — | — | — | 32.2 | — | — |
| Castor oil | 30 | 30 | 30 | 30 | 30 | 30 | 30 |
| Propylene glycol | 2 | 2 | 2 | 2 | 2 | 2 | 2 |
| Soya bean oil | 9 | 9 | 9 | 9 | 9 | 9 | 9 |

TABLE 1-continued

| Component | A | B | C | D | E | F | G |
|---|---|---|---|---|---|---|---|
| Emanon-EVE[4] | 10 | 42 | — | 10 | 10 | 23.3 | 28.7 |
| Amidet N[5] | 11.4 | 11.4 | 11.4 | 11.4 | 11.4 | 11.4 | 11.4 |
| Water | 5.4 | 5.6 | 5.7 | 5.4 | 5.4 | 6.6 | 6.2 |

International Nomenclature of Cosmetic Components:
[1]TIPA Laureth Sulphate
[2]Laureth-6 Carboxylic acid
[3]Oleth-3 Carboxylic acid
[4]Glycereth-7 Caprylate/Caprate
[5]PEG-4 Rapeseedamide Composition Appearance and Stability All the compositions D-G according to the invention are transparent with a light yellow tone and are stable after 30 days. The comparative compositions B and C have a turbid appearance and show separation after 30 days.

The stability was measured after 24 h and after 30 days, at controlled temperatures of 5° C., room temperature and 40° C.

The stability results are shown in Table 2.

TABLE 2

| Example | Stability 24 h (*) | Stability 30 days (*) |
|---|---|---|
| A | ✓ | ✓ |
| B | ✓ | X |
| C | ✓ | X |
| D | ✓ | ✓ |
| E | ✓ | ✓ |
| F | ✓ | ✓ |
| H | ✓ | ✓ |

(*) Symbol interpretation
✓: The formula is stable, it remains as a transparent single-phase formula
X: Phase separation is observed Oil Deposition The oil deposition capability on skin is one of the advantageous features of the compositions according to the invention.

Oil deposition was determined by the following method. A piece of deer skin was stirred for 5 minutes with 1 g of shower oil composition and 4 g of water, using a red dye (0.1% Sudan III) for labeling the oil. The piece of deer skin was then rinsed under running water for 30 seconds (T about 40° C.) and dried for 24 h at 20° C. and 60% relative humidity. The colorant was extracted (by stirring with 5 ml of acetone), 4 times. The solvent was left to evaporate and the extracted colorant was dissolved in 5 ml of acetone. The absorbance of the solution was measured at 502 nm (maximum absorption). Additionally, the same process was performed washing a piece of deer skin only with oil and colorant, i.e., in the absence of the surfactant system.

The concentration of the extracted colorant was calculated using the Beer-Lambert law.

It is possible to determine the percentage of oil deposition by comparing the values of oil deposition obtained from the shower oil composition with the values obtained with the sample only with oil.

The oil deposition results are shown in Table 3:

TABLE 3

| Example | Oil deposition (%) |
|---|---|
| A | 36 |
| D | 44 |

TABLE 3-continued

| Example | Oil deposition (%) |
|---|---|
| E | 57 |
| F | 55 |
| H | 47 |

The compositions according to the invention show values of oil deposition greater than the oil deposition of the comparative composition A based on the laureth-TIPA.

In summary, the compositions according to the invention involve a suitable alternative with respect to the laureth-TIPA-based compositions, formulas having the same appearance and stability parameters and showing advantages in relation to the capability to favor the oil deposition on skin being achieved.

The invention claimed is:

1. A cosmetic or dermatological composition comprising:
   a) between 10% and 34% by weight of at least one alkyl ether carboxylate of formula (I):

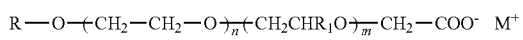

$$R-O-(CH_2-CH_2-O)_n-(CH_2CHR_1O)_m-CH_2-COO^- \quad M^+ \quad (I)$$

wherein
   R is a linear or branched, saturated or unsaturated alkyl or alkenyl group having 6 to 22 carbon atoms
   $R_1$ is an alkyl group having 1 to 4 carbon atoms
   n has a value in the range of 0 to 20
   m has a value in the range of 0 to 6
   $M^+$ is a cation selected from the group consisting of hydrogen, an alkaline metal, an alkaline earth metal, ammonium, an alkylammonium, an alkanolammonium, and a glucammonium,
   b) between 9% and 30% by weight of at least one ethoxylated glycerol ester of formula II:

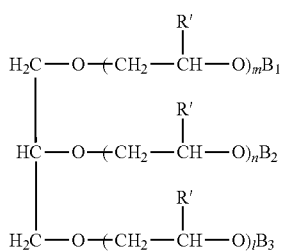

$$\begin{array}{l} H_2C-O-(CH_2-\overset{R'}{\underset{|}{CH}}-O)_m B_1 \\ HC-O-(CH_2-\overset{R'}{\underset{|}{CH}}-O)_n B_2 \\ H_2C-O-(CH_2-\overset{R'}{\underset{|}{CH}}-O)_l B_3 \end{array} \quad (II)$$

where said formula (II) comprises the components of formula i), ii), iii) and/or iv),
   i) being the component represented by formula (II), where one of the symbols $B_1$, $B_2$, $B_3$ independently represents an acyl group represented by —CO—R and the rest represents H;
   ii) being the component represented by formula (II) where two of the symbols $B_1$, $B_2$, $B_3$ independently represent an acyl group represented by —CO—R and the rest represents H;

iii) being the component represented by formula (II) where each of the symbols $B_1$, $B_2$, $B_3$ independently represents an acyl group represented by —CO—R;
iv) being the component represented by formula (II), where each of $B_1$, $B_2$ and $B_3$ represents H;
each of m, n or l independently represents a number from 0 to 40, the sum of m, n, l being in the range of 1 to 40;
R' represents H or $CH_3$;
and wherein the acyl group represented by —CO—R, R represents a linear or branched alkyl or alkenyl group having 5 to 9 carbon atoms,
c) between 20% and 50% by weight of at least one oily substance selected from animal or plant oils, hydrocarbons, esters of a higher alcohol and a higher fatty acid, fatty acids, triglycerides, fatty acid cholesterol esters, scented oils, and mixtures of any of the aforementioned components,
d) water,
e) optionally one or more emulsifiers,
f) optionally additional surfactants, and
g) optionally cosmetically or pharmaceutically acceptable excipients or active ingredients;

each of the indicated amounts being expressed as percentage by weight of the mentioned component with respect to the total weight of the active material of the composition, wherein the active material is the sum of components a, b and f.

2. The composition according to claim 1, characterized in that component b) comprises at least two different components of formula (II): one of formula (i), (ii) or (iii), and another of formula (iv); the proportion of the components [(i)+(ii)+(iii)]/(iv) by weight being between 3.0:0.3 and 0.5:3.0.

3. The composition according to claim 1, characterized in that component b) comprises components of formulas (i), (ii), (iii) and (iv); the proportion of the components [(i)+(ii)+(iii)]/(iv) by weight being between 3.0:0.3 and 0.5:3.0, and the ratio of the components (i)/(ii)/(iii) by weight being 60-90/10-35/less than 10.

4. The composition according to claim 1, characterized in that the sum of m, n and l is comprised between 1 and 20.

5. The composition according to claim 1, characterized in that the oily substance (component c)) is a plant oil.

6. The composition according to claim 5, characterized in that the plant oil is selected from the group consisting of castor oil, soya bean oil, wheat germ oil, sunflower oil and mixtures thereof.

7. The composition according to claim 1, comprising:
between 13% and 21%, by weight of component a)
between 20% and 28%, by weight of component b), and
between 30% and 45%, by weight of component c).

8. The composition according to claim 1 which only contains components a), b), c) and d).

9. A method for cleansing and/or moisturizing skin, comprising the steps of:
(1) wetting or dampening the skin,
(2) applying a sufficient amount of a composition according to claim 1 on the skin, and
(3) rinsing the skin with water.

10. The method according to claim 9, characterized in that in step (2) the composition is applied on the skin either directly or using a cleansing instrument.

11. The method according to claim 9 for cleansing and/or moisturizing skin when showering or bathing.

12. A method for the preparation of the compositions according to claim 1 comprising the following steps:
a) mixing the components a), b) and c), and optionally the components e), f) and g);
b) adjusting the pH with a NaOH solution and,
c) adding water.

13. The method according to claim 9, characterized in that in step (2) the composition is applied on the skin using brushes, sponges or meshes.

14. The method according to claim 1, wherein the at least one oily substance comprises triglycerides, wherein the triglycerides comprise natural triglycerides, including those which have been hydrogenated to reduce or eliminate unsaturations.

* * * * *